United States Patent [19]

Griffin et al.

[11] Patent Number: 4,587,956
[45] Date of Patent: May 13, 1986

[54] REVERSIBLE MAGNETIC THERAPEUTIC DEVICE AND METHOD OF USE

[76] Inventors: William D. Griffin, Rte. 2, Box 53A, Brimfield, Ill. 61517; William D. Griffin, II, 3107 W. Willow Knolls Dr., Peoria, Ill. 61614

[21] Appl. No.: 650,248

[22] Filed: Sep. 13, 1984

[51] Int. Cl.[4] .......................................... A61B 17/52
[52] U.S. Cl. ..................................................... 128/1.3
[58] Field of Search ....................................... 128/1.3

[56] References Cited

U.S. PATENT DOCUMENTS

| | | |
|---|---|---|
| 125,006 | 3/1872 | Bazault . |
| 237,939 | 2/1881 | Wilson . |
| 272,904 | 2/1883 | Russell . |
| 410,652 | 9/1889 | Scott . |
| 658,027 | 9/1900 | Steiger . |
| 781,448 | 1/1905 | McIntyre .............................. 128/1.5 |
| 3,921,620 | 11/1975 | Nakayama ............................ 128/1.3 |
| 3,943,912 | 3/1976 | Nakayama ............................ 128/1.3 |
| 4,162,672 | 7/1979 | Yazaki ................................. 128/1.3 |
| 4,240,437 | 12/1980 | Church ................................ 128/420 |
| 4,330,892 | 5/1982 | Fukushima ................................ 5/437 |

FOREIGN PATENT DOCUMENTS

| | | |
|---|---|---|
| 1215110 | 4/1960 | France . |
| 2308384 | 11/1976 | France .................................. 128/3 |
| 2339410 | 8/1977 | France .................................. 128/3 |
| 1954 | of 1874 | United Kingdom . |
| 3345 | of 1875 | United Kingdom . |
| 371 | of 1879 | United Kingdom . |
| 894095 | 2/1960 | United Kingdom . |

OTHER PUBLICATIONS

Ortopediia Traumatologiia I Protezirovanie (Moskova) (8) Aug. 1980, pp. 4-7 (Abstract on p. 7).
Voprosy Kurortologii Kultury (Moskova) (4) Jul.-Aug. 1981, pp. 28-31 (Abstract on p. 31).

*Primary Examiner*—Peter D. Rosenberg
*Attorney, Agent, or Firm*—McCaleb, Lucas & Brugman

[57] ABSTRACT

A reversible magnetic therapeutic device comprising a two-sided flexible wrapper, a plurality of magnets sufficiently sized and spaced apart across its length and width to provide a therapeutically effective two-dimensional array with all the north poles and all the south poles on opposite sides, connecting devices along opposite edges enabling it to be wrapped in sleeve form about an ailing body part optionally in north or south pole configuration modes in which all the north poles or all the south poles respectively face inwardly. The device is used by wrapping it about the ailing body part first in the north pole mode until it is pain free, and, second, in the south pole mode to restore it to a healthy condition. Magnetic flux concentration in the range of about 200 to 600 gauss per square inch provides effective therapeutic results with significant improvement up to about 6400 gauss per square inch.

10 Claims, 15 Drawing Figures

N-POLE FLUX

S-POLE FLUX

ACHILLES TENDON

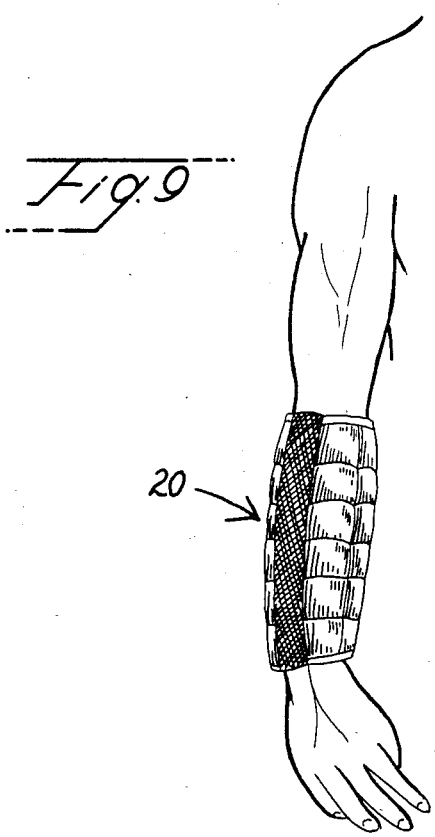
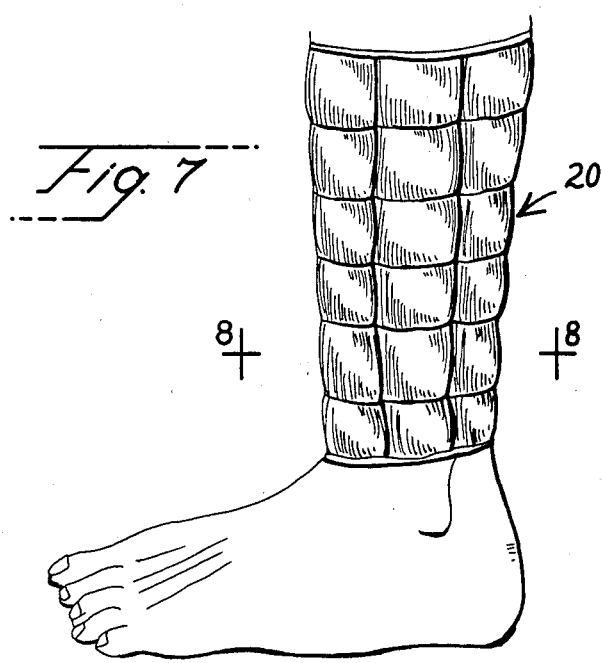
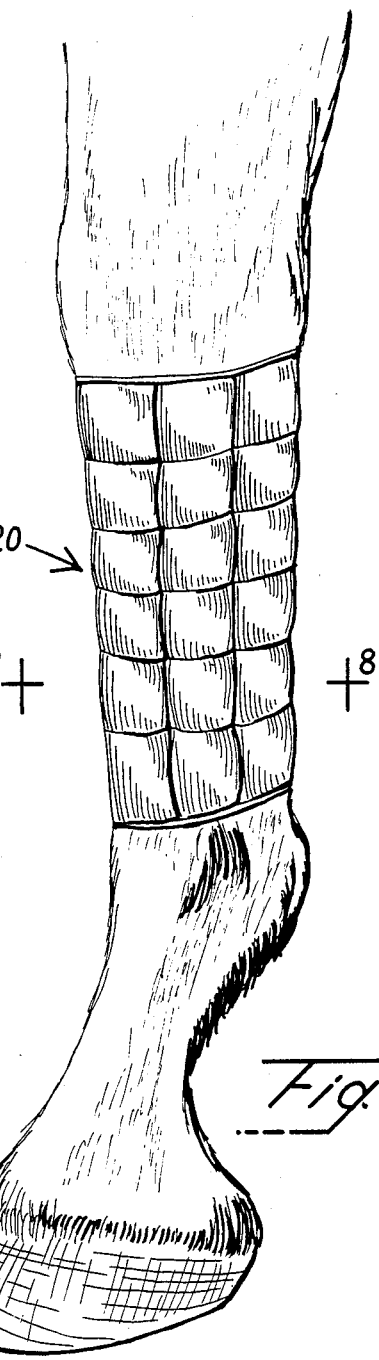

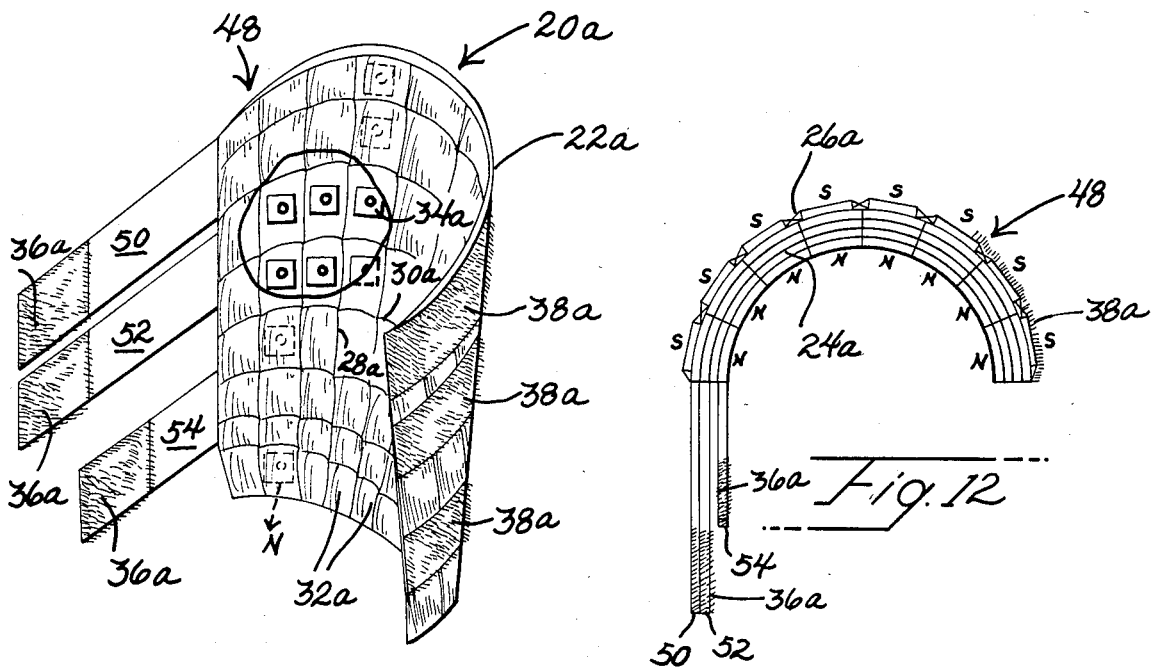
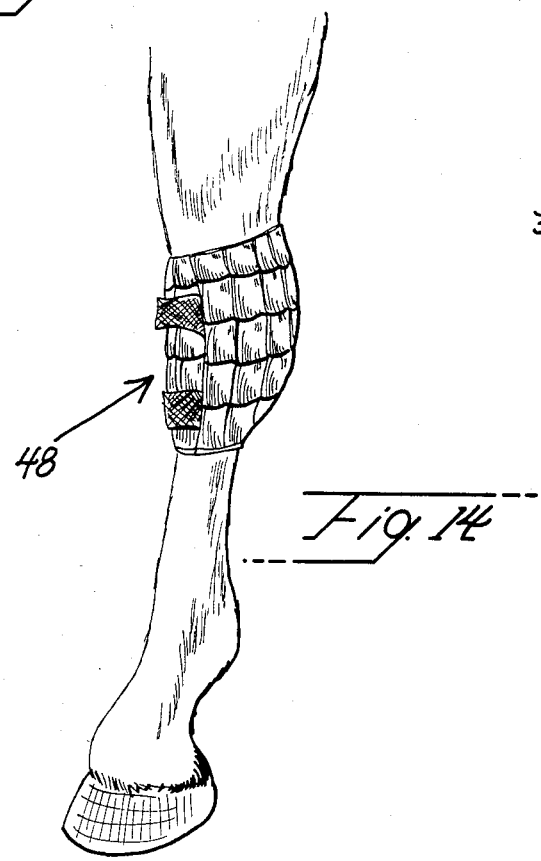
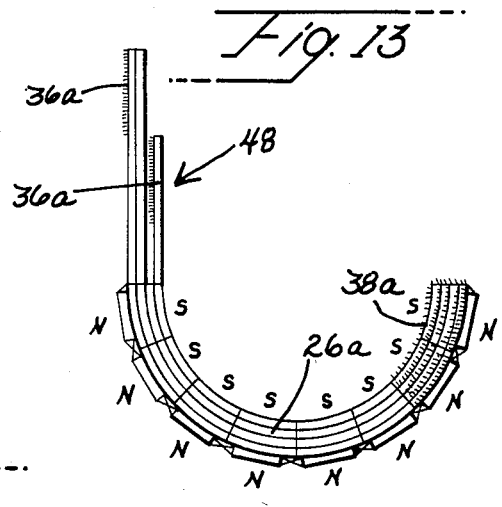

REVERSIBLE MAGNETIC THERAPEUTIC DEVICE AND METHOD OF USE

BACKGROUND OF THE INVENTION

This invention relates to a magnetic therapeutic device for humans and animals.

Strained and sprained muscles, bruised tissues and stiff or arthritic joints are common problems in both humans and animals. Conventionally these are treated by applying heat to the body part in some way, for example, by hot, wet compresses, electric heating pads, diathermy machines or hot water baths or boots.

Race horses are prime examples of valuable animals whose muscles are worked to the limit and suffer strains, sprains, and hock and knee injuries. Aside from humane considerations, a horse must not be raced when it would aggravate an injury, lest it worsen and terminate his career. On the other hand, he must be healed and ready to race as soon as possible to keep him in top form and maximize his owner's return on investment, whether the horse is raced as a business or as a sport.

There are special problems in treating leg injuries in horses, or other animals, by the conventional methods which work on humans. Immobilization for hot, wet compress treatment is not practical, nor is restricting movement for any length of time to effect diathermy treatment. Many devices have been proposed to provide hot water therapy for soreness and lameness in racehorses. For example, U.S. Pat. No. 4,183,329 describes a long, hot-water-filled trough with inclined entrance and exit ramps. U.S. Pat. Nos. 3,835,815 and 4,332,217 show an open tank into which a horse can be lowered by a hoist and sling U.S. Pat. No. 4,332,217 shows an exercising treadmill. U.S. Pat. Nos. 3,155,072; 3,234,935; and 3,272,201 show stationary water-filled boots in which the horse stands during treatment of leg injuries. This equipment is expensive, bulky, awkward, inconvenient, and restricts the horse's movements, even though some of these are described as "exercising equipment".

I have developed an improved magnetic therapeutic device and method of using it which is effective and speedy in treating a variety of human and animal ailments, especially for use on legs and arms.

The effect of magnetism on the body has been the subject of speculation for a great many years. The use of magnets in belts, belly bands, bracelets, adhesive plaster, clothing, footwear, necklaces and other items of wear or adornment has been proposed for therapeutic purposes, but the effectiveness of magnets for these purposes has been difficult to prove and it has not been widely accepted.

However, blood and other fluids circulating within the body are ionized. Sodium and potassium ions are abundant in all body fluids. Ions of many other elements are present at least in trace amounts. When flowing in a magnetic field, they, therefore, may be expected to act in the nature of an electric current and be subject to forces and electromagnetic relationships according to Fleming's Rule.

Previous proposals to apply magnetic energy to body tissues have been concerned with devices for directing magnetic flux into the tissue being treated. No significance has been attached to possible differences in therapeutic effects of flux emitting from the respective north and south poles of magnets in the aforementioned devices.

I have discovered, contrary to previous assumptions and proposals, that opposite magnetic poles have unique therapeutic effects on body tissues. These effects are significantly different, even opposed in some respects. Further, magnetic flux from either pole alone can be directed into a body part to obtain unique effects; and by applying the north and south pole fluxes sequentially, they will cure or heal a wide variety of acute and chronic ailments and injuries.

In the present state of the art, little is known about the nature of magnetism beyond the facts that unlike poles attract, like poles repel, and iron, nickel and cobalt make the best magnets; and that electric current within or without a conductor, and magnetism, are related according to the so-called "Fleming Rule". Further, the chemical, electrical and magnetic interactions within the body at the atomic, molecular and tissue cell levels are only vaguely understood. Inasmuch as blood and body fluids are electrically conductive and ionized, it is believed they produce magnetic fields at least at the molecular or atomic levels in much the same manner as electrical currents consisting of moving electrons produce magnetic fields according to the Fleming Rule.

According to accepted findings, the outer membrane of normal blood and tissue cells, and the outer fiber covering of nerves, have an electrogalvanic potential across them. The external surface of the nerve outer fiber cover has a charge which is positive relative to the interior. When the tissues in a body part are subjected to trauma, infection, disease, or are severed, the potential across that outer nerve fiber cover increases, automatically sending a sensation of pain to the brain.

Unfortunately, there is an opposite, conflicting, electrogalvanic relationship between injured and diseased tissue and blood on the one hand, and nerves on the other hand. The rate of healing of injured tissue increases if the electrogalvanic potential across the tissue outer membrane is increased. This improves blood circulation, and speeds up exchange of oxygen and waste products in the tissue. But where tissue is painful, pain increases if the potential across the nerve outer fiber coating is increased.

Thus, any means or method of increasing the potential across both the outer membrane of the tissue and adjacent outer nerve fiber coating would be counterproductive because increase in pain would limit mobility and exercise which are essential for healing and full restoration of muscles and joints. Ideally, before any attempt is made to heal and restore body tissue, it must be free of pain.

I have discovered that flux from a north pole of a magnet if applied in effective levels in the order of at least 200 gauss per square inch has a sedator effect, reduces pain, mobilizes calcium, relieves muscle spasms, increases joint mobility and lowers the pH of the affected tissues. By contrast, flux from a south pole of a magnet stimulates circulation, speeds healing time, strengthens tissues, and raises the pH to a weak alkaline condition characterizing healthy tissue. I believe, without at this time being able to explain the exact electrogalvanic and magnetic interactions at the atomic or molecular levels, that the north pole flux may reduce the electrogalvanic potential across the nerve sheaths in the affected tissue to a value substantially below that recognized by the brain as a pain signal; and that the south pole flux, if applied subsequently, does not raise the potential to a value which the brain would recognize as a pain signal, thus it can effect healing while enabling normal exercise without pain.

With these principles in mind, I have found that, by first applying north pole flux of a substantial magnitude completely around the periphery of a muscle, tendon or joint, it will effectively eliminate pain and mobilize the patient; then, by applying south pole flux in the same manner while the patient exercises normally, it will rebuild and strengthen these body parts in a shorter recovery time than is possible with conventional treatment apparatus and methods.

SUMMARY OF THE INVENTION

A general object of the present invention is to provide a therapeutic device and method for applying magnetic flux to an ailing or injured human or animal body part.

Another object is to provide a magnetic therapeutic device in the form of a reversible wrapper having a plurality of magnets spaced apart across the height and width thereof with their magnetic axes oriented substantially perpendicularly to the plane of the wrapper and with all the north poles on one side and all the south poles on the other side, and connecting or adhering means along opposite edges of the wrapper effective to hold the wrapper in sleeve or tubular form snugly conformable to a body part with either the south or the north poles selectively facing inwardly depending on the specific therapeutic benefit desired.

Another object is to provide such a therapeutic device in which the magnets are spaced and sized to provide an overall average flux concentration on either the north or south pole side of 200 to 6400 gauss per square inch, and preferably in the range of about 200 to 600 gauss per square inch.

Another object is to provide such a therapeutic device in which the wrapper comprises a plurality of laminated sheets sewed or otherwise adhered together to provide separate pockets between them for individual magnets.

Another object is to carry out a therapeutic treatment method for an ailing, painful body part comprising the steps of exposing the part completely around its periphery first to north pole magnetic flux directed radially therein from all directions until a marked reduction in pain is obtained, followed by exposing the part completely around its periphery to opposite, south pole magnetic flux similarly directed radially therein until the part is restored to a healthy, normal condition.

Another object is to carry out such a therapeutic treatment method in which the north and south pole magnetic fluxes are directed into the body part with a magnetic intensity of up to 6400 gauss per square inch, and preferably in the range of about 200 to 600 gauss per square inch.

Another object is to carry out such a therapeutic treatment on an ailing, painful body part by providing a flexible wrapper having magnets spaced apart across the height and width thereof, with all the magnetic axes perpendicular to the wrapper and all the north and south poles facing opposite sides of the wrapper, and applying the device in a two-step operation, first, by wrapping the device in sleeve-like form about the body part with the north pole ends of the magnets disposed inwardly until the pain subsides, and, second, reversing the device and wrapping it about the body part with the south pole ends of the magnets disposed inwardly until the body part is restored to a healthy condition.

BRIEF DESCRIPTION OF THE DRAWING

Other objects and advantages will be apparent from the accompanying drawings in which:

FIG. 7 is a side view of a human leg with the device positioned to treat a strained or sprained Achilles tendon, and showing the magnetic flux saturation in the tissues being treated;

FIG. 9 is a view showing the device positioned to treat a human forearm;

FIG. 10 is a view showing the device positioned to treat the tendons in the shinbone or cannonbone region of a horse;

FIG. 11 is a perspective view of a modified form of the device mode for elastic wear on a joint;

FIG. 12 is a top view of the device shown in FIG. 10 in an N-pole mode, that is with the north poles of the magnets facing inwardly;

FIG. 13 is a view of the device shown in FIGS. 11 and 12, in the S-pole mode, reversed with respect to FIG. 12; and FIG. 14 is a view of the device of FIGS. 10 and 11 applied to the hock joint of a horse, enabling treatment while the animal is free to exercise normally.

Like parts are referred to by like reference numerals throughout the figures of the drawings.

DETAILED DESCRIPTION OF THE DRAWINGS

Figure 1:
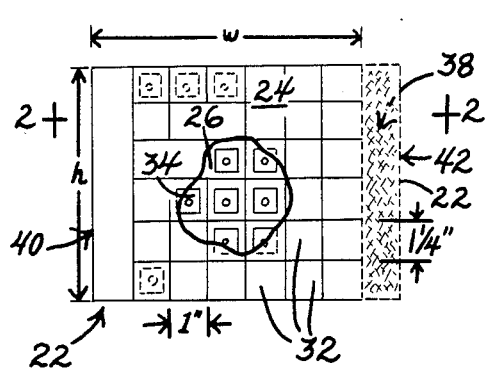
FIG. 1 is a plan view of a magnetic therapeutic device embodying the present invention.
Figure 2:
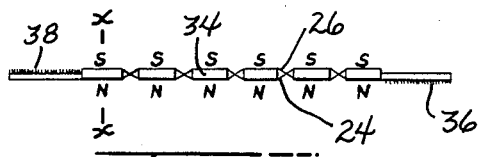
FIG. 2 is a sectional view of FIG. 1 taken on line 2—2.

Referring now to the specific embodiments of the invention shown in the drawings, the therapeutic device shown in FIGS. 1-10. is generally designated 20 and comprises a flexible wrapper 22 of laminated construction consisting of two sheets 24 and 26 of non-allergic cloth, leather, plastic or other flexible material. The sheets are sewed or otherwise adhered together along vertical and horizontal lines 28 and 30 to provide individual compartments or pockets 32 for permanent magnets 34 which are thereby spaced apart across the height and width of the wrapper and with their magnetic axes X-X (FIGS. 2 and 4) perpendicular to the plane of the wrapper. All the magnets are polarized in the same direction, that is, all the N-poles are on one side of the wrapper, and all the S-poles are on the other.

Figure 6:
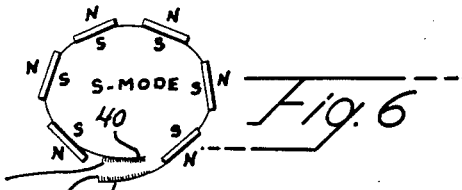
FIG. 6 is a view of the device in the S-pole mode, reversed with respect to FIG. 5.
Figure 5:
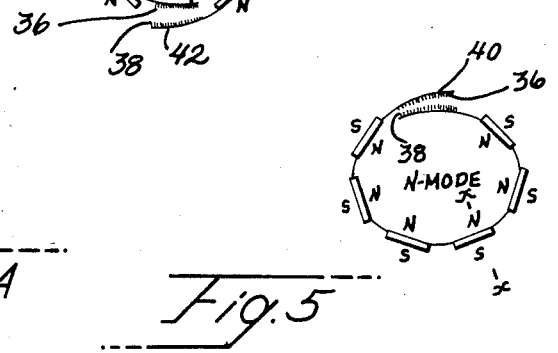
FIG. 5 is a view of the device in the N-pole mode, that is, in a circular configuration with the north poles of the magnets facing inwardly.

Connecting means are provided along opposite edges of the wrapper effective to hold it as a sleeve or tube snugly conforming to the body part being treated, in either the N- or P-mode optional configurations shown in FIGS. 5 and 6 respectively.

Specifically, releasable, mutually-adherent fastener members 36 and 38 of the so-called loop and hook type are provided along opposite edges 40, 42 and on opposite sides of the wrapper. These consist of loop-like fiber elements in one of the fastener members 36, 38 and hook-like fiber elements in the other. They are pressure-sensitive in that they cling and adhere tightly to one another when pressed together but are repeatedly, manually separable. This type of fastener is sometimes referred to as "Velcro" and is described in detail in U.S. Pat. Nos. 2,714,437; 3,009,235 and 3,562,044. Any other type fastener which is reversible and adjustable to fit the device snugly about the body part may be used.

Figure 8:
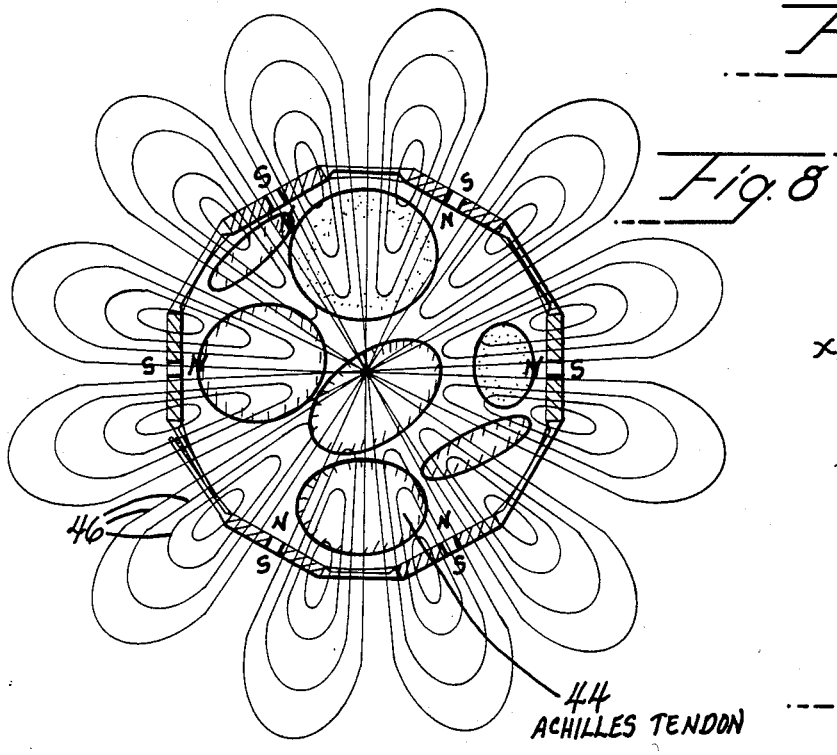
FIG. 8 is an approximate sectional view of FIG. 7 taken on line 8—8 with magnetic flux lines schemetically superimposed to illustrate how the device may be used to treat a strained Achilles tendon in either a human or an animal.

The wrapper 22 should be of sufficient width (between the edges 40, 42) to substantially encircle and enclose the body part being treated. Preferably, the array of magnets should completely surround the part so a plurality of diametrically opposed magnets direct effective levels of flux inwardly from all directions, as shown in FIG. 8. Where the wrapper is intended for general use on different size body parts, the width should be made for the largest size and it may be overlapped on smaller sizes.

The height of the device should be substantial to cover the entire axial length of the ailing body part or joint, and preferably with some excess length at each end to assure complete saturation of the tissues with magnetic flux. Multiple circumferential rows of magnets reinforce and supplement one another to provide therapeutic benefits completely beyond the order of magnitude of the benefits which could be obtained with a relatively narrow band or bracelet having a single row of magnets girdling the ailing part.

FIGS. 7, 9 and 10 show examples of the device 20 applied respectively to the leg and forearm of a human, and to the lower shin region of a horse. Note that, in each case, the sleeve-like, tubular configuration extends for a substantial distance along the axis of the leg or arm; this should extend beyond the part needing treatment by a significant amount to assure complete and adequate exposure to effective levels of magnetic flux.

In treating a strained Achilles tendon 44 of a human or animal, the device 20 will be wrapped snugly about the lower leg, in the N-pole configuration shown in FIGS. 5 and 8. External views are shown in FIGS. 7 and 10. A representative cross-section is shown in FIG. 8, with the N-pole magnetic flux lines 46 completely saturating the Achilles tendon and neighboring tissues. The patient, human or animal, is completely ambulatory, and can move about as freely as the soreness in the tendon permits. Typically the soreness subsides and completely disappears within a relatively short time, usually a few hours, as contrasted with the extended time required for the soreness to go away by itself. When the pain is gone, the device 20 is removed, reversed, and replaced in the S-pole configuration shown in FIG. 6 in which the south pole flux saturates the tissues and begins the healing process by increasing circulation in the strained tendon and surrounding tissues and nerves.

Similarly, as shown in FIG. 9, sprained or strained muscles in a patient's forearm may be treated by first wrapping the device 20 about the forearm in the N-pole configuration mode until the soreness is gone, then reversing it to the S-pole mode for the final, healing step.

Another embodiment of the invention, generally designated 48, is shown in FIGS. 11-14. This is a special adaptation, for a flexible joint such as a human elbow, a human or horse knee, or a horse hock, and has inbuilt flexibility to accomodate relative, normal movement of the bones adjoining the joint. It is used for treating an arthritic or stiffened condition of the joint. The embodiment 48 comprises a flexible wrapper 22a of laminated construction consisting of two sheets 24a and 26a of nonallergic cloth, leather, plastic or the like. As with the previously-described embodiment, the sheets are sewed or otherwise adhered together along vertical and horizontal lines 28a, 30a to provide separate compartments or pockets 32a for permanent magnets 34a which are spaced apart across the height and width of the wrapper, with their magnetic axes perpendicular to the plane of the wrapper. All the N-poles are on one side of the wrapper and all the S-poles are on the other.

In this case, the connecting means includes forwardly extending, elastic straps 50, 52 and 54 having hook or loop ("Velcro") pads 36a engageable with complementary hook or loop pads 38a along opposite edges of the wrapper. The elastic straps 50, 52 and 54 may be of selectively different lengths as shown, or may be the same length.

The alternate device 20a may be applied to a joint such as the hock joint shown in FIG. 14 and it can be worn for extended periods of time with comfort because of the elasticity provided by the straps and the flexibility provided by the wrapper. As with the previously described device 20, device 20a may be applied first to a joint by turning it to the N-pole configuration mode shown in FIG. 12 with the N-poles facing inwardly until pain is relieved, after which it may be reversed and applied in the S-pole configuration mode shown in FIG. 13 with the S-poles facing inwardly.

Figure 3:
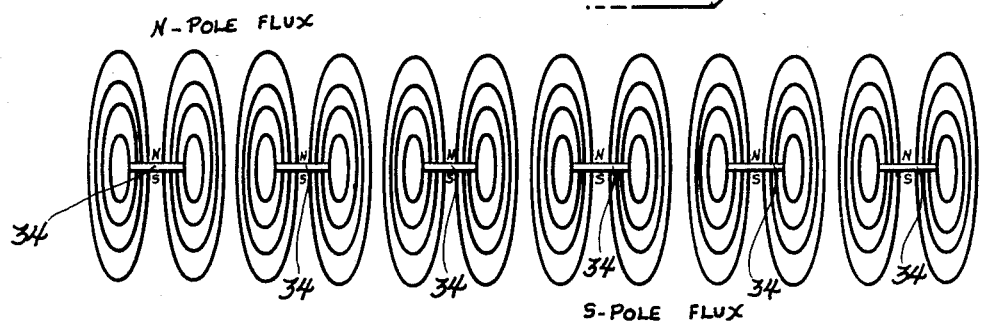
FIG. 3 is a schematic diagram of the respective north and south magnetic flux fields illustrated for a single row of magnets in the device.

FIG. 3 is a schematic representation of the respective N-pole and S-pole flux fields existing on opposite sides of the array of magnets 34 (or 34a). One or the other of these magnetic flux fields can be "beamed" into the tissue or joint being treated, simply by placing the device in the N- or S-mode configuration.

I have found a very substantially different therapeutic effect when the device is applied in the N-pole mode as shown in FIGS. 5 and 12 on the one hand; or in the S-pole mode as shown in FIGS. 6 and 13 on the other hand. The sides of the device may be suitably coded by colors, letters or numerals to readily indicate which side is which. Although, as stated above, the exact reason is not fully understood, the N-mode configuration has a sedator effect, reduces pain, relieves muscle spasms, increases joint motility, mobilizes calcium, and lowers the pH in the affected tissue; and the S-pole mode stimulates circulation, speeds healing time, strengthens ailing tissues, and increases the pH toward a normal, healthy, slightly acid condition.

As a typical condition, to treat a painful or stiff human elbow, human or horse knee, or the hock joint of a horse or other animal, in accordance with the present invention, the device 20a shown in FIGS. 11-14 will first be wrapped about the joint in the N-pole mode configuration shown in FIG. 12, with all the north poles of the magnets facing inwardly. After a period of time which can vary from three hours to three days depending on the chronicity of the ailment, the pain is relieved, so the joint can be subjected to normal exercise without hurting when stress is applied.

The device will then be reversed, and rewrapped about the joint in the S-pole mode configuration shown in FIG. 13 with the south poles of all the magnets facing inwardly. This increases the circulation, facilitates the natural healing process of exchanging oxygen for the waste products of the ailment or injury generated by the healing process. The healing process is greatly facilitated and shortened by enabling the person or animal to be fully mobile and therefore free of pain enabling him to exercise normally. An ailing tendon or joint of a horse free to move normally while wearing the device heals much faster than when it is restricted to stable care required for diathermy or hot water bath treatment or when immobilized following surgery. As described, the therapeutic magnetic devices 20 and 20a are simple and compact, easy to apply and remove, they allow the patient complete freedom of movement, and are effective first to remove pain and then to heal an ailing joint or tissue with absolutely no adverse side effects when used in the special two-step N-pole/S-pole sequence described.

Figure 1A:
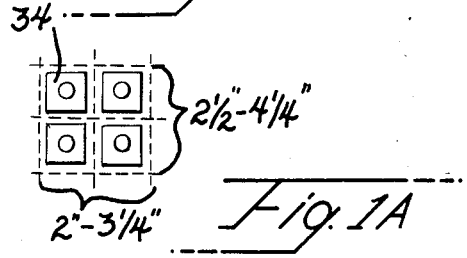
FIG. 1A is a fragmentary, enlarged view of FIG. 1.
Figure 4:
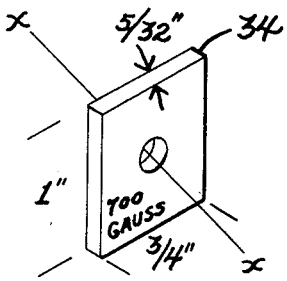
FIG. 4 is an enlarged perspective view of one of the magnets used in the device.

One particular type of magnet 34 or 34a which has been used successfully in this invention has the advantage of being a standard item available from stock at most magnet suppliers in small and large quantities at a few cents apiece. As shown in FIG. 4, it is 1"×3/4"×5/32" with a 9/16" diameter center hole. It is of the ceramic type, rated at approximately 700 gauss,. One source for magnets of this type is Edmund Scientific Co., Barrington, N.J. As shown in Fig. 1A, I have varied widths and heights of the individual pockets 32 from 1" to 1⅝" and 1¼" to 2⅜" respectively. The farthest and closest of these spacings therefore provided a range of about 200 to 600 gauss per square inch respectively and these were used in the clinical tests reported herein.

As a general observation, magnetic flux levels in the above-mentioned range of about 200 to 600 gauss per square inch provided therapeutic benefits of the same general order of magnitude. Very large increases in magnetic flux levels, up to about 6400 gauss per square inch, provided some significant increases in the speed that these benefits were obtained. The 6400 gauss flux level was obtained with individual magnets 34 or 34a having 8000 gauss flux rating each and with the compartments 32 positioning them as closely together as possible. Increases in the average flux level above 6400 did not significantly improve or accelerate the therapeutic benefits of the device; further, these high flux levels required the use of relatively expensive alloy magnets which are not easily available.

Summarizing the above comments about magnetic flux levels, optimum results appear to be obtainable in the 200 to 600 gauss per square inch range inasmuch as significant and improved therapeutic benefits are obtainable in substantially less time than is possible with conventional treatments, and readily available and relatively cheap 700 gauss ceramic magnets will provide that range of flux levels. Above the 600 gauss level, there is not sufficient advantage either in quality or speed of treatment to justify the substantially increased cost of the special alloy, high flux magnets required. And, above the intensive 6400 gauss level, no additional benefits are obtained, it appearing that some kind of saturation point is reached.

Notwithstanding the above descriptions of the particular magnets 34 or 34a which have been used successfully in this invention, other flux ranges, both below 200 and above 6400 gauss per square inches, may prove beneficial for some patients with certain kinds of illnesses and ailments.

Injuries involving a joint usually produce post traumatic rheumatism or arthritis. If this device is used promptly after an injury occurs, the secondary effects within the joint are lessened and in some cases stopped completely. This rheumatic or arthritic condition is the most disabling side effect of all bone and cartilage injuries in a human or animal joint. It is not the injury to the bone or cartilage that ends an athlete's career but the arthritic side effects.

The N-pole mode shown in FIGS. 5 and 8 also has the property of hindering and at times stopping the deterioration and inflammation caused by common athletic training injuries if applied as a precautionary measure regularly after exercise. This is true in both human and equine athletes.

While the S-pole mode flux treatment shown in FIG. 6 has a strengthening effect and accelerates the healing process in muscles, ligaments, tendons, and joints, it also strengthens pain so should never be applied initially while the parts are sore or painful. It is essential that it be preceded by the N-pole treatment until pain subsides.

If the body part is not painful, treatment in the S-pole mode (FIG. 6) can be used on a healthy limb during training and will cause a natural strengthening of the area treated and a large number of common injuries can be avoided.

The device is particularly effective in the treatment of bowed tendons in the equine athlete and torn or ruptured tendons in humans. It causes the tendons to tighten and strengthen themselves. The effect is also beneficial in old tendon injuries and will cause a tightening of the tendon and a decrease in swelling. Although it may not return completely to its pre-injury state, as is the case with a fresh injury treated by this method, the sooner the injury is treated the more likely it will return to its original, healthy condition. Continued frequent treatment will eliminate recurrence of the problem.

Clinical tests verifying the efficacy of the device have been carried out on a large number of animal and human patients, the earlier tests being performed on applicant's own racehorses under carefully controlled conditions, and later tests being performed on human patients in applicant's medical practice where a careful follow-up was possible.

EXAMPLES

Therapeutic devices 20 and 20a were made as shown, using magnets 34 of 700 gauss induction strength each, held in individual compartments or pockets 32 which spaced the magnets apart vertically and horizontally sufficiently to provide an average magnetic strength of about 230 gauss per square inches of the wrapper. While lower magnetic strengths are effective, results will be slower so in the interest of carrying out the treatments with reasonable despatch, I believe that for all practical purposes the lower limit of flux concentration should be at least 200 gauss per square inches. I have found that by increasing the strengths of the individual magnets or putting them closer together, beneficial effects of the treatments may be speeded up in many cases. However, there appears to be a practical upper limit to the maximum strength of the magnetic field which is effective. The upper limit appears to be in the neighborhood of 6400 gauss per square inch; as stated above, any increase in magnetic strength above that value will not be accompanied by a proportional increase in the healing rate. Thus, I believe that, for practical purposes, the useful range of effective magnetic field strength is between and 200 and 6400 gauss per square inches, while a good, all around compromise would be in the neighborhood of 200 to 6400 gauss per square inches for this is easily provided by adjusting the spacings of readily obtainable 700-gauss individual magnets which are in abundant supply at prices of only a few cents apiece.

In every one of the following cases, where the ailing body part was painful, the device was first applied in the N-pole mode with the north poles facing inwardly to direct a concentrated north pole flux into the part as shown in FIG. 8 or 12 until the pain was stopped. It was then removed, reversed and reapplied in the S-pole mode with the south poles facing inwardly as shown in FIG. 6 or 13 to saturate the joint with south pole flux until it was healed.

The device has been found to be effective, even in some cases involving bone chips, where conventional techniques have called for surgery and extended convalescence often resulting in termination of a horse's racing career despite the best of post-operative care.

In one example, X-ray examination of the horse Blazing Jubilee revealed a chipping of the bone in the left, rear hock joint. Conventional treatment for this would have been surgical removal with a six month layoff. Even with this the veterinarian felt there would be only a 10% chance of recovery because of the arthritic side effects of this type of injury.

Magnetic field therapy according to the present invention was employed daily and the horse continued on light training with steady improvement of his lameness. Four months later a re-X-ray of the joint was performed to determine if heavy training might be started. Upon examination of the horse and the X-rays, the veterinarian pronounced the horse fit and noted that the joint had completely healed with a total lack of any arthritic involvement in the joint. The horse then returned to a heavy training and racing schedule.

Another racehorse, Jubilee Rogue, suffered a tendon injury in his right front leg—diagnosed by the veterinarian as a torn right front outside flexor tendon.

For the next 48 hours the leg was enclosed in the present device, in the N-pole mode with complete elimination of pain. The horse was then put on light exercise with the device applied to the leg in S-pole mode for the next 48 hours. The horse was then returned to normal exercise and training and daily treatments of N-pole magnetic exposure on days of hard training and S-pole exposure on days of light training and rest.

One week following the injury, the horse returned to the races. An injury of this type usually requires a 4–6 week rest, followed by a 4–6 week conditioning before racing again.

Three weeks after returning to the races, the horse won, lowering his best winning time by four seconds.

Further, extensive animal studies were carried out on applicant's racehorses where treatment was needed and their healing progress closely monitored by the attending trainers and veterinarians. One hundred and fifty individual tendon, hock and knee injuries consisting of strains, sprains and bruises serious enough to require layoffs from racing were treated with 80% overall effective results. The criterion of successful therapy used by the trainers and veterinarians was, "Did the horse return to racing and did he race physically sound?" The results are tabulated below for different kinds of injuries treated with the device and method of the present invention, and a comparison is provided based on veterinary experience in conventional treatment of comparable injuries, which would involve either leaving them untreated and letting nature heal it, or performing surgery where that would be indicated by conventional practice. These are compared below.

TABLE I

| | Time required to return to racing | |
|---|---|---|
| Injuries requiring layoff from racing | With present device and method (Actual) | Estimated if left untreated or with conventional surgery |
| Lesion of bowed tendon | 3 weeks | 6 weeks to 2 months |
| Lesion of suspensory ligaments | 1 week | 4 weeks to never |
| Check Cig Strain | 1 week | 4 weeks to never |
| Lesions of the hockjoint | 3 weeks | Severely injured hocks require surgery. Racing career ended. |
| Arthritis of Hock Joint | 4–8 weeks | Surgery. Career ended. |
| Bucked shin joint | 2 weeks | Three months after surgery. |
| Lesion of knee | Remains racing, with daily treatments | Variable. Severe injuries require surgery with racing career ended. |

Clinical tests on human patients with careful follow-ups were made in applicant's Peoria, Ill. medical office. Eighty-two patients with acute ailments or injuries, and 161 patients with chronic ailments or injuries, in ages ranging 20 to 80, were treated. Table II shows the different kinds of acute injuries for which the device was tested.

TABLE II

| ACUTE INJURIES | |
|---|---|
| Acute Symptoms | Number of Patients |
| Myositis | 10 |
| Traumatic Myositis (Bruise) | 15 |
| Sprains | 5 |
| Strains | 7 |
| Hematomas | 20 |
| Back Strains | 30 |
| | 82 |

Pain was associated with each of these injuries. The device 20 or 20a, as appropriate for the treatment indicated, was initially wrapped about the body part in the N-pole mode, the patient being instructed to wear the device continuously. The initial, N-pole phase required from 1½ hour to four days to obtain pain relief, depending on the severity of the injury, the age and general health of the patient, and the patient's ability or willingness to cooperate. For minor acute injuries, pain was relieved in 1½ to three hours. For major acute injuries, pain was relieved in one to four days. Most of the major acute injuries had pain relief in 48 hours where the magnetic device was worn 16 hours per day. Where the device was worn 24 hours per day, the patients reported pain relief in one to two days.

Table III shows different kinds of chronic injuries for which the device was tested.

TABLE III

| CHRONIC INJURIES | |
|---|---|
| Chronic Symptoms | Number of Patients |
| Myositis | 50 |
| Arthritis | 25 |
| Back Strain | 26 |
| Joint Stiffness | 50 |
| Neuralgia | 10 |
| | 161 |

All the above patients were in constant pain.

As described for acute symptoms, these patients with chronic symptoms were first treated with the device in N-pole mode until pain was relieved. It was then reversed to the S-pole mode, resulting in increased circulation, strengthening of the tissues, and promoting healing.

For these chronic ailments, many which had been very long standing, the device when used as described provided substantial improvements in comfort and well being for 90% of the patients treated.

It is extremely important in the practice of this invention that the joint or tissue being treated be saturated, uniformly, from all radial directions, completely around the periphery of the ailing part, with effective levels of the north or south pole magnetic flux being used. This magnetic flux saturation from all radial directions is illustrated in FIG. 8. By contrast, we have found that localized "patch" applications of single magnets, or groups of magnets, to one or even opposite sides of a joint or tissue does not provide the desired uniform magnetic field and is not effective. To illustrate this important concept by examples which are not as effective as this invention, a single magnet applied topically on one side of ailing tissue, as disclosed in Yazaki U.S. Pat. No. 4,162,672, does not work as rapidly or effectively as the present invention. Another example is a localized group of magnets applied on one or two sides of ailing tissue, as disclosed in Nakayama U.S. Pat. Nos. 3,921,620 and 3,943,912; this likewise, does not work as rapidly as effectively, and as definitely as the present invention. It is extremely important that the magnetic flux, of one pole only, be directed uniformly from all radial angles into the body part being treated, as shown in FIG. 8.

The above described devices and methods of using them relieve pain and heal a wide variety of human and animal injuries and ailments. Numerous and various other arrangements and methods can readily be devised in keeping with the principles disclosed by those skilled in the art without departing from the spirit and scope of the invention.

The embodiments of the present invention in which an exclusive property or privilege is claimed are defined as follows:

1. A reversible magnetic therapeutic device for enclosing an animal or human ailing body part to direct a therapeutically effective uniform magnetic flux of selected exclusively north or south pole polarity into the body part from all radial directions completely around the periphery thereof comprising:
   a two-sided flexible wrapper sized to enclose the body part in either of two sleeve-like optional configurations with one or the other side of the wrapper engaging the body part;
   reversible connecting means along opposite edges of the wrapper effective to hold said wrapper as a sleeve or tube conforming to the body part in either of said optional sleeve-like configurations; and
   a plurality of magnets supported in the wrapper sufficiently sized and disposed in rows and columns completely across both the height and width thereof between said opposite edges, to provide a therapeutically effective, two-dimensional magnetic array with the north-south axes of the magnets oriented substantially perpendicularly to the plane of the wrapper and with all the north poles on one side of the wrapper and all the south poles on the other side;
   whereby a selected high uniform, therapeutically effective north or south pole flux can be directed radially into the ailing body part completely around the periphery thereof by applying the wrapper about the body part with the north or south poles of the magnets selectively facing inwardly toward the body part completely around the body part and extending beyond the ailing portion thereof at both ends of the sleeve or tube.

2. A reversible magnetic therapeutic device according to claim 1 in which the average flux level of the array of magnets is above about 200 gauss per square inch.

3. A reversible magnetic therapeutic device according to claim 1 in which the average flux level of the array of magnets is in the range of about 200 to about 600 gauss per square inch.

4. A reversible magnetic therapeutic device according to claim 1 in which the average flux level of the array of magnets is in the range of about 200 to about 6400 gauss per square inch.

5. A reversible magnetic therapeutic device according to claim 1 in which the wrapper comprises a lamination of at least two flexible sheets having separate compartments for individual magnets.

6. A therapeutic treatment method for an ailing, painful animal or human body part, the steps of:
   (a) exposing the part substantially completely around the periphery thereof to a therapeutically effective level of north pole magnetic flux directed radially therein for a sufficient duration and of sufficient magnetic intensity to obtain a marked reduction in pain; and
   (b) exposing the part completely around the periphery thereof to a therapeutically effective level of south pole magnetic flux directed radially therein from a plurality of diametrically opposed directions for a sufficient duration and of sufficient magnetic intensity to restore the part to a healthy, normal condition.

7. In a therapeutic treatment method of a body part according to claim 6, exposing the part in each of Steps (a) and (b) to an average magnetic flux of at least 200 gauss per square inch.

8. In a therapeutic treatment method of a body part according to claim 6, exposing the part in each of Steps (a) and (b) to an average magnetic flux in the range of about 200 to 600 gauss per square inch.

9. In a therapeutic treatment method of a body part according to claim 6, exposing the part in each of Steps (a) and (b) to an average magnetic flux in the range of about 200 to 6400 gauss per square inch.

10. In a therapeutic treatment method of treating an ailing body part with a flexible wrapper supporting magnets sufficiently sized and spaced across the height and width thereof to provide a therapeutically effective two-dimensional array with their magnetic axes oriented substantially perpendicularly to the plane of the wrapper and with all the north poles on side of the wrapper and all the south poles on the other side, said method comprising the steps of:

(a) applying said wrapper as a sleeve completely enclosing the body part with the north poles of the magnets turned inwardly, for a sufficient length of time to obtain a marked reduction in pain; and (b) removing and reversing the wrapper and reapplying it as a sleeve completely enclosing the body part with the south poles of the magnets turned inwardly, for a sufficient length of time to obtain a marked improvement in the health condition of the body part.

* * * * *